(12) United States Patent
Gillespie et al.

(10) Patent No.: US 7,538,064 B2
(45) Date of Patent: May 26, 2009

(54) ISOMERIZATION CATALYST AND PROCESS

(75) Inventors: Ralph D. Gillespie, Friendswood, TX (US); Feng Xu, Buffalo Grove, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 12/147,064

(22) Filed: Jun. 26, 2008

(65) Prior Publication Data

US 2008/0280755 A1 Nov. 13, 2008

Related U.S. Application Data

(60) Division of application No. 11/304,521, filed on Dec. 15, 2005, now Pat. No. 7,414,007, which is a continuation-in-part of application No. 10/869,252, filed on Jun. 16, 2004, now abandoned, which is a division of application No. 10/243,524, filed on Sep. 13, 2002, now abandoned.

(51) Int. Cl.
- *B01J 27/00* (2006.01)
- *B01J 27/185* (2006.01)
- *B01J 23/00* (2006.01)
- *B01J 23/40* (2006.01)
- *B01J 23/42* (2006.01)
- *B01J 23/56* (2006.01)
- *B01J 23/44* (2006.01)

(52) U.S. Cl. .................. 502/208; 502/213; 502/305; 502/313; 502/316; 502/326; 502/327; 502/332; 502/333; 502/334; 502/339; 502/351

(58) Field of Classification Search ............. 502/208, 502/213, 305, 313, 316, 326, 327, 332–334, 502/339, 351
See application file for complete search history.

(56) References Cited

U.S. PATENT DOCUMENTS

| | | | |
|---|---|---|---|
| 5,120,898 A | 6/1992 | Baba et al. | 585/750 |
| 5,214,017 A | 5/1993 | Angstadt et al. | 502/204 |
| 5,310,868 A | 5/1994 | Angstadt et al. | 585/721 |
| 5,345,026 A * | 9/1994 | Chang et al. | 585/700 |

(Continued)

FOREIGN PATENT DOCUMENTS

WO   WO 03/013722 A1   2/2003

(Continued)

OTHER PUBLICATIONS

"Effect of preparation method and selective poisoning on the performance of platinum supported on tungstated zrconia catalyst for alkane isomerization," Gustavo Larsen et al. Applied Catalysis A: General 148 (1996), pp. 155-166.*

(Continued)

*Primary Examiner*—Patricia L Hailey
(74) *Attorney, Agent, or Firm*—Maryann Maas

(57) ABSTRACT

A catalyst and process is disclosed to selectively upgrade a paraffinic feedstock to obtain an isoparaffin-rich product for blending into gasoline. The catalyst comprises a support of a tungstated oxide or hydroxide of a Group IVB (IUPAC 4) metal, a phosphorus component, and at least one platinum-group metal component which is preferably platinum. The catalyst has a structure other than a hetropoly anion structure.

11 Claims, 10 Drawing Sheets

U.S. PATENT DOCUMENTS

| | | | |
|---|---|---|---|
| 5,422,327 A | 6/1995 | Soled et al. | 50/242 |
| 5,489,733 A | 2/1996 | Soled et al. | 585/740 |
| 5,510,309 A | 4/1996 | Chang et al. | 502/308 |
| 5,648,589 A | 7/1997 | Soled et al. | 585/734 |
| 5,719,097 A | 2/1998 | Chang et al. | 502/325 |
| 5,780,382 A | 7/1998 | Chang et al. | 502/309 |
| 5,780,703 A | 7/1998 | Chang et al. | 585/732 |
| 5,854,170 A | 12/1998 | Chang et al. | 502/308 |
| 5,902,767 A | 5/1999 | Kresge et al. | 502/308 |
| 6,080,904 A | 6/2000 | Chang et al. | 585/751 |
| 6,107,235 A * | 8/2000 | Matsuzawa | 502/217 |
| 6,118,036 A | 9/2000 | Zinnen | 585/738 |
| 6,124,232 A | 9/2000 | Chang et al. | 502/308 |
| 6,184,430 B1 | 2/2001 | Venkatesh et al. | 585/750 |
| 6,818,589 B1 | 11/2004 | Gillespie | 502/326 |
| 6,977,322 B2 | 12/2005 | Gillespie | 585/750 |
| 7,304,199 B2 | 12/2007 | Xu et al. | 585/734 |
| 7,399,896 B2 * | 7/2008 | Gillespie et al. | 585/740 |
| 7,414,007 B2 * | 8/2008 | Gillespie et al. | 502/208 |
| 2003/0105171 A1 | 6/2003 | Subramanian et al. | 518/715 |
| 2004/0256289 A1 * | 12/2004 | Gillespie et al. | 208/113 |

FOREIGN PATENT DOCUMENTS

WO     2004/024319     *     3/2004

OTHER PUBLICATIONS

"Pd-promoted WOx/ZrO2 catalysts: Characterization and catalytic activity for n-butane isomerization," M. Occiuzzi et al. Applied Catalysis A: General 351 (2008), pp. 29-35.*

"Modified zirconia solid acid catalysts for organic synthesis and transformations," Benjaram M. Reddy et al. Journal of Molecular Catalysis A: Chemical 225 (2005), pp. 71-78.*

"Platinum- and iron-doubly promoted tungstated zirconia catalyst for n-butane isomerization reaction," She-Tin Wong et al. Applied Catalysis A: General 296 (2005), pp. 90-99.*

"Characteristics of Pt/WO3/CeO2/ZrO2 catalysts for catalytic reduction of NO by CO," Hai-ou Zhu et al. Applied Catalysis B: Environmental 86 (2009), pp. 87-92.*

* cited by examiner

US 7,538,064 B2

ISOMERIZATION CATALYST AND PROCESS

CROSS-REFERENCE TO RELATED APPLICATIONS

This application is a Division of application Ser. No. 11/304,521, filed Dec. 15, 2005, which in turn is a Continuation-In-Part of application Ser. No. 10/869,252, filed Jun. 16, 2004, now abandoned, which in turn is a Division of application Ser. No. 10/243,524 filed Sep. 13, 2002, now abandoned, the contents of which are hereby incorporated by reference in their entirety.

FIELD OF THE INVENTION

This invention relates to an improved catalytic composite and process for the conversion of hydrocarbons, and more specifically for the selective upgrading of a paraffinic feedstock by isomerization.

BACKGROUND OF THE INVENTION

The widespread removal of lead antiknock additive from gasoline and the rising fuel-quality demands of high-performance internal-combustion engines have compelled petroleum refiners to install new and modified processes for increased "octane," or knock resistance, in the gasoline pool. Refiners have relied on a variety of options to upgrade the gasoline pool, including higher-severity catalytic reforming, higher FCC (fluid catalytic cracking) gasoline octane, isomerization of light naphtha and the use of oxygenated compounds. Such key options as increased reforming severity and higher FCC gasoline octane result in a higher aromatics content of the gasoline pool at the expense of low-octane heavy paraffins.

Refiners are also faced with supplying reformulated gasoline to meet tightened automotive emission standards. Reformulated gasoline differs from the traditional product in having a lower vapor pressure, lower final boiling point, increased content of oxygenates, and lower content of olefins, benzene and aromatics. Benzene content generally is being restricted to 1% or lower, and is limited to 0.8% in U.S. reformulated gasoline. Gasoline aromatics content is likely to be lowered, particularly as distillation end points (usually characterized as the 90% distillation temperature) are lowered, since the high-boiling portion of the gasoline which thereby would be eliminated usually is an aromatics concentrate. Since aromatics have been the principal source of increased gasoline octanes during the recent lead-reduction program, severe restriction of the benzene/aromatics content and high-boiling portion will present refiners with processing problems. These problems have been addressed through such technology as isomerization of light naphtha to increase its octane number, isomerization of butanes as alkylation feedstock, and generation of additional light olefins as feedstock for alkylation and production of oxygenates using FCC and dehydrogenation. This issue often has been addressed by raising the cut point between light and heavy naphtha, increasing the relative quantity of naphtha to an isomerization unit.

Additionally, instead of reforming, the isomerization of longer chain hydrocarbons such as $C_7$ and $C_8$ hydrocarbons into branched hydrocarbons of higher octane could be used to increase the octane number of fuels without increasing the amount of aromatics. However, many isomerization catalysts suffer significant disadvantages when applied to the longer chain hydrocarbons. A principal problem is the generation of byproducts such as cracked hydrocarbon materials. The cracking decreases the amount of long chain paraffins available for isomerization and reduces the ultimate yield.

Several catalysts for isomerization are known, and a family of tungstated zirconia catalysts have been used. For example, U.S. Pat. Nos. 5,510,309 B1, 5,780,382 B1, 5,854,170, and 6,124,232 B1 teach methods of making an acidic solid having a Group IVB (IUPAC 4) metal oxide modified with an oxyanion of a Group VIB (IUPAC 6) metal such as zirconia modified with tungstate. U.S. Pat. No. 6,184,430 B1 teaches a method of cracking a feedstock by contacting the feedstock with a metal-promoted anion modified metal oxide catalyst where the metal oxide is one or more of $ZrO_2$, $HfO_2$, $TiO_2$ and $SnO_2$, the modifier is one or more of $SO_4$ and $WO_3$, and the metal is one or more of Pt, Ni, Pd, Rh, Ir, Ru, Mn, and Fe.

Others have added a noble metal such as platinum to the tungstated zirconia catalysts above, see U.S. Pat. Nos. 5,719,097; 6,080,904 B1; and 6,118,036 B1. A catalyst having an oxide of a Group IVB (IUPAC 4) metal modified with an anion or oxyanion of a Group VIB (IUPAC 6) metal and a Group IB (IUPAC 11) metal or metal oxide is disclosed in U.S. Pat. No. 5,902,767. In U.S. Pat. Nos. 5,648,589 and 5,422,327, a catalyst having a Group VIII (IUPAC 8, 9, and 10) metal and a zirconia support impregnated with silica and tungsten oxide and a process of isomerization using the catalyst is disclosed. A process for forming a diesel fuel blending component uses an component uses an acidic solid catalyst having a Group IVB (IUPAC 4) metal oxide modified with an oxyanion of Group VIB (IUPAC 6) metal and iron or manganese in U.S. Pat. No. 5,780,703 B1.

U.S. Pat. Nos. 5,310,868 and 5,214,017 teach catalyst compositions containing sulfated and calcined mixtures of (1) a support containing an oxide or hydroxide of IUPAC 4 (Ti, Zr, Hf), (2) an oxide or hydroxide of IUPAC 6 (Cr, Mo, W); IUPAC 7 (Mn, Tc, Re), or IUPAC 8, 9, and 10 (Group VIII) metal, (3) an oxide or hydroxide of IUPAC 11 (Cu, Ag, Au), IUPAC 12 (Zn, Cd, Hg), IUPAC 3 (Sc, Y), IUPAC 13 (B, Al, Ga, In, Tl), IUPAC 14 (Ge, Sn, Pb), IUPAC 5 (V, Nb, Ta), or IUPAC 6 (Cr, Mo, W), and (4) a metal of the lanthanide series.

U.S. Pat. No. 5,489,733 teaches a catalyst having a zirconium hydroxide support, a Group VIII metal, and a heteropolyacid selected from the group consisting of the exchanged aluminum salt of 12-tungstophosphoric acid, the exchanged salt of 12-tungstosilicic acid, and mixtures thereof. The catalyst is used for isomerization processes having a feed comprising $C_n$ or $C_n+$ wherein n=4.

Applicant has developed a more effective catalyst that has proved to be surprisingly superior to those already known for the isomerization of hydrocarbons and especially $C_7$ and $C_8$ hydrocarbons.

SUMMARY OF THE INVENTION

A purpose of the present invention is to provide an improved catalyst and process for hydrocarbon conversion reactions. Another purpose of the present invention is to provide improved technology to upgrade naphtha to gasoline. A more specific purpose is to provide an improved catalyst and process for the isomerization of full boiling point range naphtha to obtain a high-octane gasoline component. This invention is based on the discovery that a catalyst containing a phosphorous compound such as a phosphorous oxide, a phosphorous hydroxide, a phosphorous halide, a phosphorous oxyhalide, a phosphorous carbonate, a phosphorous nitrate, a phosphorous sulfate, or a phosphorus component present within the support plus a platinum-group component provides superior performance and stability in the isomerization of full boiling point range naphtha to increase its isoparaffin content. The catalyst has a structure other than a heteropoly anion structure.

A broad embodiment of the present invention is directed to a catalyst comprising a tungstated support of an oxide or hydroxide of a Group IVB (IUPAC 4) metal, preferably zirconium oxide or hydroxide, at least a first component which is a phosphorus component, and at least a second component being a platinum-group metal component. The second component preferably consists of a single platinum-group metal, which is most preferably a platinum component. The catalyst optionally contains an inorganic-oxide binder, especially alumina. The catalyst has a structure other than a heteropoly anion structure.

An additional embodiment of the invention is a method of preparing the catalyst of the invention by tungstating the Group IVB (IUPAC 4) metal oxide or hydroxide, incorporating a first component which is a phosphorous component, and the second component which is a platinum-group metal, and preferably binding the catalyst with a refractory inorganic oxide. The catalyst has a structure other than a heteropoly anion structure.

In another aspect, the invention comprises converting hydrocarbons using the catalyst of the invention. In yet another embodiment, the invention comprises the isomerization of isomerizable hydrocarbons using the catalyst of the invention. The hydrocarbons preferably comprise a full boiling point range naphtha which is isomerized to increase its isoparaffin content and octane number as a gasoline blending stock.

These as well as other embodiments will become apparent from the detailed description of the invention.

DETAILED DESCRIPTION OF THE INVENTION

Figure 1:
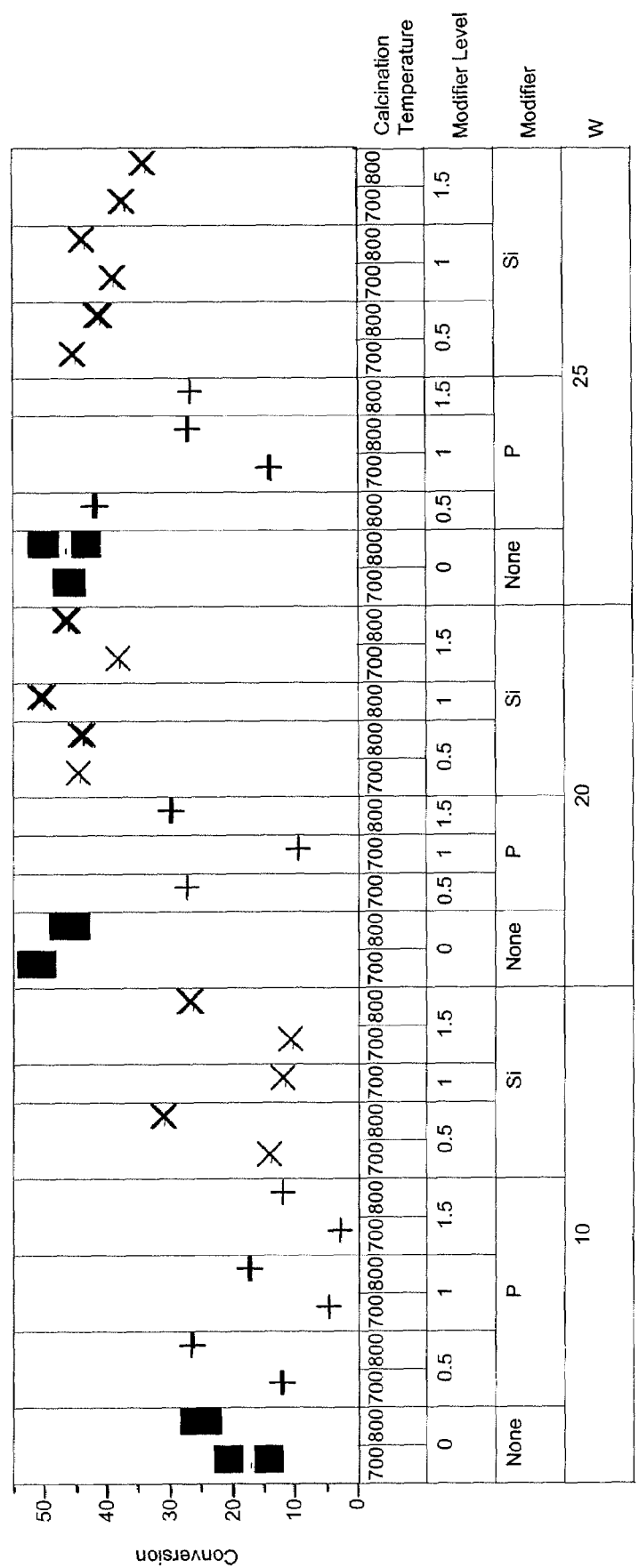
FIG. 1 is a plot of the conversion of n-heptane achieved by selected catalysts made in Example 1.

The support material of the catalyst of the present invention comprises an oxide or hydroxide of a Group IVB (IUPAC 4) metal, see Cotton and Wilkinson, Advanced Inorganic Chemistry, John Wiley & Sons (Fifth Edition, 1988) and including zirconium, titanium and hafnium. Preferably, the metal is selected from zirconium and titanium, with zirconium being especially preferred. The preferred zirconium oxide or hydroxide is converted via calcination to crystalline form. Tungstate is composited on the support material to form, it is believed without so limiting the invention, a mixture of Brönsted and Lewis acid sites. A component of at least one Group IVA (IUPAC 14) component, Group VA (IUPAC 15) component, or mixtures thereof, is incorporated into the composite by any suitable means. A platinum-group metal component is added to the catalytic composite by any means known in the art to effect the catalyst of the invention, e.g., by impregnation. Optionally, the catalyst is bound with a refractory inorganic oxide. The support, tungstate, metal components, and optional binder may be composited in any order effective to prepare a catalyst useful for the conversion of hydrocarbons, and particularly the isomerization of hydrocarbons.

Production of the support of the present catalyst may be based on a hydroxide of a Group IVB (IUPAC 4) metal as raw material. For example, suitable zirconium hydroxide is available from MEI of Flemington, N.J. Alternatively, the hydroxide may be prepared by hydrolyzing metal oxy-anion compounds, for example $ZrOCl_2$, $ZrO(NO_3)_2$, $ZrO(OH)NO_3$, $ZrOSO_4$, $TiOCl_2$ and the like. Note that commercial $ZrO(OH)_2$ contains a significant amount of Hf, about 1 weight percent. Zirconium alkoxides such as zirconyl acetate and zirconium propoxide may be used as well. The hydrolysis can be effected using a hydrolyzing agent such as ammonium hydroxide, sodium hydroxide, potassium hydroxide, sodium sulfate, $(NH_4)_2HPO_4$ and other such compounds known in the art. The metal oxy-anion component may in turn be prepared from available materials, for example, by treating $ZrOCO_3$ with nitric acid. The hydroxide as purchased or generated by hydrolysis preferably is dried at a temperature of from about 100° C. to 300° C. to vaporize volatile compounds.

A tungstated support is prepared by treatment with a suitable tungstating agent to form a solid strong acid. Liquid acids whose strength is greater than sulfuric acid have been termed "superacids". A number of liquid superacids are known in the literature including substituted protic acids, e.g., trifluoromethyl substituted $H_2SO_4$, triflic acid and protic acids activated by Lewis acids (HF plus $BF_3$). While determination of the acid strength of liquid superacids is relatively straightforward, the exact acid strength of a solid strong acid is difficult to directly measure with any precision because of the less defined nature of the surface state of solids relative to the fully solvated molecules found in liquids. Accordingly, there is no generally applicable correlation between liquid superacids and solid strong acids such that if a liquid super acid is found to catalyze a reaction, there is no corresponding solid strong acid which one can automatically choose to carry out the same reaction. Therefore, as will be used in this specification, "solid strong acids" are those that have an acid strength greater than sulfonic acid resins such as Amberlyst®-15. Additionally, since there is disagreement in the literature whether some of these solid acids are "superacids" only the term solid strong acid as defined above will be used herein. Another way to define a solid strong acid is a solid comprising of interacting protic and Lewis acid sites. Thus, solid strong acids can be a combination of a Bronsted (protonic) acid and a Lewis acid component. In other cases, the Bronsted and Lewis acid components are not readily identified or present as distinct species, yet they meet the above criteria.

Tungstate ions are incorporated into a catalytic composite, for example, by treatment with ammonium metatungstate in a concentration usually of about 0.1 to 20 mass percent tungsten and preferably from about 1 to 15 mass percent tungsten. Compounds such as metatungstic acid, sodium tungstate, ammonium tungstate, ammonium paratungstate, which are capable of forming tungstate ions upon calcining, may be employed as alternative sources. Preferably, ammonium metatungstate is employed to provide tungstate ions and form a solid strong acid catalyst. The tungstate content of the finished catalyst generally is in the range of about 0.5 to 30 mass-%, and preferably is from about 1 to 25 mass-% on an elemental basis. The tungstate composite is dried, preferably followed by calcination at a temperature of about 450° C. to 1000° C. particularly if the tungstanation is to be followed by incorporation of the platinum-group metal.

A first component, comprising one or more of the Group IVA (IUPAC 14) components, Group VA (IUPAC 15) components, or mixtures thereof, is another essential component of the present catalyst. Included in the Group IVA components are silicon, germanium, tin, and lead. Included in the Group VA components are nitrogen, phosphorus, arsenic, antimony, and bismuth. Preferred elements include silicon, phosphorus, and germanium, with silicon being the most preferred. The first component may, in general, be present in the catalytic composite in any catalytically available form such as the elemental metal, a compound such as the oxide, hydroxide, halide, oxyhalide, carbonate or nitrate. The first component is preferably an oxide, an intermetallic with platinum, a sulfate, or in the zirconia lattice. The materials are generally calcined between 450° C. and 1000° C., with a preferred temperature of above 600° C. and at about 800° C., and thus in the oxide form. Although it is not intended to so restrict the present invention, it is believed that best results are obtained when the first component is present in the composite in a form wherein substantially all of the first component is in an oxidation state above that of the elemental state such as in the form of the oxide, oxyhalide or halide or in a mixture thereof and the subsequently described oxidation and reduction steps that are preferably used in the preparation of the instant catalytic composite are specifically designed to achieve this end. The first component can be incorporated into the catalyst in any amount which is catalytically effective, suitably from about 0.01 to about 10 mass-% first component in the finished catalyst on an elemental basis. Best results usually are achieved with about 1 to about 5 mass-% of the first component, calculated on an elemental basis.

The first component is incorporated in the catalytic composite in any suitable manner known to the art, such as by coprecipitation, coextrusion with the porous carrier material, or impregnation of the porous carrier material either before, after, or simultaneously with tungstate though not necessarily with equivalent results. For ease of operation, it is preferred to simultaneously incorporate the first component with the tungstate, however, the first component and the tungstate are each individual materials. It is most preferred to incorporate the incorporate the platinum-group metal component last. As to the first component and the platinum-group metal, the order of addition between the two does not have a significant impact.

One method of depositing the first component involves impregnating the support with a solution (preferably aqueous) of a decomposable compound of the first component. By decomposable is meant that upon heating, the compound is converted to element or oxide with the release of byproducts. Illustrative of the decomposable compounds without limitation are complexes or compounds such as, nitrates, halides, sulfates, acetates, organic alkyls, hydroxides, and the like compounds. Conditions for decomposition include temperatures ranging from about 200° C. to about 400° C. The first component can be impregnated onto the carrier either prior to, simultaneously with, or after the platinum-group metal component, although not necessarily with equivalent results. If a sequential technique is used, the composite can be dried or dried and calcined in between impregnations.

A second component, a platinum-group metal, is an essential ingredient of the catalyst. The second component comprises at least one of platinum, palladium, ruthenium, rhodium, iridium, or osmium; platinum is preferred, and it is especially preferred that the platinum-group metal consists essentially of platinum. The platinum-group metal component may exist within the final catalytic composite as a compound such as an oxide, sulfide, halide, oxyhalide, etc., in chemical combination with one or more of the other ingredients of the composite or as the metal. Amounts in the range of from about 0.01 to about 2 mass-% platinum-group metal component, on an elemental basis, are effective, and from about 0.1 to 1 mass-% platinum-group metal component, on an elemental basis, are preferred. Best results are obtained when substantially all of the platinum-group metal is present in the elemental state.

The second component, a platinum-group metal component, is deposited on the composite using the same means as for the first component described above. Illustrative of the decomposable compounds of the platinum group metals are chloroplatinic acid, ammonium chloroplatinate, bromoplatinic acid, dinitrodiamino platinum, sodium tetranitroplatinate, rhodium trichloride, hexa-amminerhodium chloride, rhodium carbonylchloride, sodium hexanitrorhodate, chloropalladic acid, palladium chloride, palladium nitrate, diamminepalladium hydroxide, tetraamminepalladium chloride, hexachloroiridate (IV) acid, hexachloroiridate (III) acid, ammonium hexachloroiridate (III), ammonium aquohexachloroiridate (IV), ruthenium tetrachloride, hexachlororuthenate, hexaammineruthenium chloride, osmium trichloride and ammonium osmium chloride. The second component, a platinum-group component, is deposited on the support either before, after, or simultaneously with tungstate and/or the first component though not necessarily with equivalent results. It is preferred that the platinum-group component is deposited on the support either after or simultaneously with tungstate and/or the first component. Again, each of the components, the tungstate, the first component, and the second component are each individual materials.

In addition to the first and second components above, the catalyst may optionally further include a third component of iron, cobalt, nickel, rhenium or mixtures thereof. Iron is preferred, and the iron may be present in amounts ranging from about 0.1 to about 5 mass-% on an elemental basis. The third component, such as iron, may function to lower the amount of the first component needed in the optimal formulation. The third component may be deposited on the composite using the same means as for the first and second components as described above. When the third component is iron, suitable compounds would include iron nitrate, iron halides, iron sulfate and any other soluble iron compound.

The catalytic composite described above can be used as a powder or can be formed into any desired shapes such as pills, cakes, extrudates, powders, granules, spheres, etc., and they may be utilized in any particular size. The composite is formed into the particular shape by means well known in the art. In making the various shapes, it may be desirable to mix the composite with a binder. However, it must be emphasized that the catalyst may be made and successfully used without a binder. The binder, when employed, usually comprises from about 0.1 to 50 mass-%, preferably from about 5 to 20 mass- %, of the finished catalyst. Refractory inorganic oxide are suitable binders. Examples of binders without limitation are silica, aluminas, silica-alumina, magnesia, zirconium and mixtures thereof. A preferred binder material is alumina, with eta—and/or especially gamma-alumina being favored. Usually the composite and optional binder are mixed along with a peptizing agent such as HCl, $HNO_3$, KOH, etc. to form a homogeneous mixture which is formed into a desired shape by forming means well known in the art. These forming means include extrusion, spray drying, oil dropping, marumarizing, conical screw mixing, etc. Extrusion means include screw extruders and extrusion presses. The forming means will determine how much water, if any, is added to the mixture. Thus, if extrusion is used, then the mixture should be in the form of a dough, whereas if spray drying or oil dropping is used, then enough water needs to be present in order to form a slurry. These slurry. These particles are calcined at a temperature of about 260° C. to about 650° C. for a period of about 0.5 to about 2 hours.

The catalytic composites of the present invention either as synthesized or after calcination can be used as catalysts in hydrocarbon conversion processes. Calcination is required, for example, to form zirconium oxide from zirconium hydroxide. Hydrocarbon conversion processes are well known in the art and include cracking, hydrocracking, alkylation of both aromatics and isoparaffins, isomerization, polymerization, reforming, dewaxing, hydrogenation, dehydrogenation, transalkylation, dealkylation, hydration, dehydration, hydrotreating, hydrodenitrogenation, hydrodesulfurization, methanation, ring opening, and syngas shift processes. Specific reaction conditions and the types of feeds, which can be used in these processes, are set forth in U.S. Pat. Nos. 4,310,440 and 4,440,871, which are hereby incorporated by reference. A preferred hydrocarbon conversion process is the isomerization of paraffins.

In a paraffin isomerization process, common naphtha feedstocks boiling within the gasoline range contain paraffins, naphthenes, and aromatics, and may comprise small amounts of olefins. Feedstocks which may be utilized include straight-run naphthas, natural gasoline, synthetic naphthas, thermal gasoline, catalytically cracked gasoline, partially reformed naphthas or raffinates from extraction of aromatics. The feedstock essentially is encompassed by the range of a full-range naphtha, or within the boiling point range of 0° C. to 230° C.

The principal components of the preferred feedstock are alkanes and cycloalkanes having from 4 to 10 carbon atoms per molecule, especially those having from 7 to 8 carbon atoms per molecule. Smaller amounts of aromatic and olefinic hydrocarbons also may be present. Usually, the concentration of $C_7$ and heavier components is more than about 10 mass-% of the feedstock. Although there are no specific limits to the total content in the feedstock of cyclic hydrocarbons, the feedstock generally contains between about 2 and 40 mass-% of cyclics comprising naphthenes and aromatics. The aromatics contained in the naphtha feedstock, although generally amounting to less than the alkanes and cycloalkanes, may comprise from 0 to 20 mass-% and more usually from 0 to 10 mass-% of the total. Benzene usually comprises the principal aromatics constituent of the preferred feedstock, optionally along with smaller amounts of toluene and higher-boiling aromatics within the boiling ranges described above.

Contacting within the isomerization zones may be effected using the catalyst in a fixed-bed system, a moving-bed system, a fluidized-bed system, or in a batch-type operation. A fixed-bed system is preferred. The reactants may be contacted with the bed of catalyst particles in either upward, downward, or radial-flow fashion. The reactants may be in the liquid phase, a mixed liquid-vapor phase, or a vapor phase when contacted with the catalyst particles, with excellent results being obtained by application of the present invention to a primarily liquid-phase operation. The isomerization zone may be in a single reactor or in two or more separate reactors with suitable means therebetween to ensure that the desired isomerization temperature is maintained at the entrance to each zone. Two or more reactors in sequence are preferred to enable improved isomerization through control of individual reactor temperatures and for partial catalyst replacement without a process shutdown.

Isomerization conditions in the isomerization zone include reactor temperatures usually ranging from about 25° C. to 300° C. Lower reaction temperatures are generally preferred in order to favor equilibrium mixtures having the highest concentration of high-octane highly branched isoalkanes and to minimize cracking of the feed to lighter hydrocarbons. Temperatures in the range of about 100° C. to about 250° C. are preferred in the process of the present invention. Reactor operating pressures generally range from about 100 kPa to 10 Mpa absolute, preferably between about 0.3 and 4 Mpa. Liquid hourly space velocities range from about 0.2 to about 25 $hr^{-1}$, with a range of about 0.5 to 10 $hr^{-1}$ being preferred.

Hydrogen is admixed with or remains with the paraffinic feedstock to the isomerization zone to provide a mole ratio of hydrogen to hydrocarbon feed of from about 0.01 to 20, preferably from about 0.05 to 5. The hydrogen may be supplied totally from outside the process or supplemented by hydrogen recycled to the feed after separation from the reactor effluent. Light hydrocarbons and small amounts of inert material such as nitrogen and argon may be present in the hydrogen. Water should be removed from hydrogen supplied from outside the process, preferably by an adsorption system as is known in the art. In a preferred embodiment, the hydrogen to hydrocarbon mole ratio in the reactor effluent is equal to or less than 0.05, generally obviating the need to recycle hydrogen from the reactor effluent to the feed.

Upon contact with the catalyst, at least a portion of the paraffinic feedstock is converted to desired, higher octane, isoparaffin products. The catalyst of the present invention provides the advantages of high activity and improved stability.

The isomerization zone generally also contains a separation section, optimally comprising one or more fractional distillation columns having associated appurtenances and separating lighter components from an isoparaffin-rich product. Optionally, a fractionator may separate an isoparaffin concentrate from a cyclics concentrate with the latter being recycled to a ring-cleavage zone.

Preferably part or all of the isoparaffin-rich product and/or the isoparaffin concentrate are blended into finished gasoline along with other gasoline components from refinery processing including, but not limited to, one or more of butanes, butenes, pentanes, naphtha, catalytic reformate, isomerate, alkylate, polymer, aromatic extract, heavy aromatics, gasoline from catalytic cracking, hydrocracking, thermal cracking, thermal reforming, steam pyrolysis and coking, oxygenates such as methanol, ethanol, propanol, isopropanol, tert-butyl alcohol, sec-butyl alcohol, methyl tertiary butyl ether, ethyl tertiary butyl ether, methyl tertiary amyl ether and higher alcohols and ethers, and small amounts of additives to promote gasoline stability and uniformity, avoid corrosion and weather problems, maintain a clean engine and improve driveability.

The following examples serve to illustrate certain specific embodiments of the present invention. These examples should not, however, be construed as limiting the scope of the invention as set forth in the claims. There are many possible other variations, as those of ordinary skill in the art will recognize, which are within the scope of the invention.

EXAMPLE 1

Catalyst samples of Tables 1, 2, and 3 were prepared starting with zirconium hydroxide that had been prepared by precipitating zirconyl nitrate with ammonium hydroxide at 65° C. The zirconium hydroxide was dried at 120° C., ground to 40-60 mesh. Multiple discrete portions of the zirconium hydroxide were prepared. Solutions of either ammonium metatungstate or a metal salt (component 1) were prepared and added to the portions of zirconium hydroxide. The materials were agitated briefly and then dried with 80° C. to 100° C. air while rotating. The impregnated samples were then dried in a muffle oven at 150° C. for 2 hours under air. Solutions of a metal salt (component 2, where component 2 is not the same as component 1) were prepared and added to the dried materials. The samples were briefly agitated and dried while rotating. The samples were then calcined at 600° C. to 850° C. for 5 hours. The final impregnation solutions of chloroplatinic acid were prepared and added to the solids. The samples were agitated and dried while rotating as before. The samples were finally calcined at 525° C. in air for 2 hours. In Table 1 below, it can be seen that the catalysts were made at silicon or phosphorous modifier levels of 0.25 mass-%, 0.5 mass-%, 0.75 mass-%, 1 mass-%, and 1.5 mass-%; tungstate levels of 10 mass-%, 15 mass-%, 20 mass-%, and 25 mass-%; and calcination temperatures of 600° C., 700° C., and 800° C. The catalysts also contained 0.4 mass-% platinum. Table 1 represents a total of 120 different catalysts that were made.

In Table 2 below, it can be seen that the catalysts were made at nominal phosphorus modifier levels of 0.025 mass-%, 0.05 mass-%, and 0.1 mass-%; nominal tungstate levels of 20 mass-%, 22.5 mass-%, 25 mass-%, and 30 mass-%; and calcination temperatures of 700° C., 800° C., and 850° C. The catalysts also contained nominally 0.4 mass-% platinum. Table 2 represents a total of 28 different catalysts that were made.

In Table 3 below, it can be seen that the catalysts were made at nominal germanium modifier levels of 0.5 mass-%, 1 mass-%, and 2.5 mass-%; nominal tungstate levels of 10 mass-%, 15 mass-%, and 20 mass-%; and calcination temperatures of 600° C., 700° C., and 800° C. The catalysts also contained nominally 0.4 mass-% platinum. Table 3 represents a total of 27 different catalysts that were made.

TABLE 1

| | | | | | | | | | | |
|---|---|---|---|---|---|---|---|---|---|---|
| Si (mass %) | 0.25 | 0.25 | 0.25 | 0.25 | 0.5 | 0.5 | 0.5 | 0.5 | 0.75 | 0.75 |
| W (mass %) | 10 | 15 | 20 | 25 | 10 | 15 | 20 | 25 | 10 | 15 |
| Calc. Temp ° C. | 600 | 600 | 600 | 600 | 600 | 600 | 600 | 600 | 600 | 600 |
| Si (mass %) | 0.25 | 0.25 | 0.25 | 0.25 | 0.5 | 0.5 | 0.5 | 0.5 | 0.75 | 0.75 |
| W (mass %) | 10 | 15 | 20 | 25 | 15 | 25 | 10 | 20 | 10 | 25 |
| Calc. Temp ° C. | 700 | 700 | 700 | 700 | 700 | 700 | 700 | 700 | 700 | 700 |
| Si (mass %) | 0.25 | 0.25 | 0.25 | 0.25 | 0.5 | 0.5 | 0.5 | 0.5 | 0.75 | 0.75 |
| W (mass %) | 10 | 15 | 20 | 25 | 15 | 25 | 10 | 20 | 10 | 25 |
| Calc. Temp ° C. | 800 | 800 | 800 | 800 | 800 | 800 | 800 | 800 | 800 | 800 |
| P (mass %) | 0.25 | 0.25 | 0.25 | 0.25 | 0.5 | 0.5 | 0.5 | 0.5 | 0.75 | 0.75 |
| W (mass %) | 10 | 15 | 20 | 25 | 10 | 15 | 20 | 25 | 10 | 15 |
| Calc. Temp ° C. | 600 | 600 | 600 | 600 | 600 | 600 | 600 | 600 | 600 | 600 |
| P (mass %) | 0.25 | 0.25 | 0.25 | 0.25 | 0.5 | 0.5 | 0.5 | 0.5 | 0.75 | 0.75 |
| W (mass %) | 10 | 15 | 20 | 25 | 15 | 25 | 10 | 20 | 10 | 25 |
| Calc. Temp ° C. | 700 | 700 | 700 | 700 | 700 | 700 | 700 | 700 | 700 | 700 |
| P (mass %) | 0.25 | 0.25 | 0.25 | 0.25 | 0.5 | 0.5 | 0.5 | 0.5 | 0.75 | 0.75 |
| W (mass %) | 10 | 15 | 20 | 25 | 15 | 25 | 10 | 20 | 10 | 25 |
| Calc. Temp ° C. | 800 | 800 | 800 | 800 | 800 | 800 | 800 | 800 | 800 | 800 |
| Si (mass %) | 0.75 | 0.75 | 1 | 1 | 1 | 1 | 1.5 | 1.5 | 1.5 | 1.5 |
| W (mass %) | 20 | 25 | 10 | 15 | 20 | 25 | 10 | 15 | 20 | 25 |
| Calc. Temp ° C. | 600 | 600 | 600 | 600 | 600 | 600 | 600 | 600 | 600 | 600 |
| Si (mass %) | 0.75 | 0.75 | 1 | 1 | 1 | 1 | 1.5 | 1.5 | 1.5 | 1.5 |
| W (mass %) | 20 | 15 | 15 | 20 | 10 | 25 | 15 | 20 | 25 | 10 |
| Calc. Temp ° C. | 700 | 700 | 700 | 700 | 700 | 700 | 700 | 700 | 700 | 700 |
| Si (mass %) | 0.75 | 0.75 | 1 | 1 | 1 | 1 | 1.5 | 1.5 | 1.5 | 1.5 |
| W (mass %) | 20 | 15 | 15 | 20 | 10 | 25 | 15 | 20 | 25 | 10 |
| Calc. Temp ° C. | 800 | 800 | 800 | 800 | 800 | 800 | 800 | 800 | 800 | 800 |
| P (mass %) | 0.75 | 0.75 | 1 | 1 | 1 | 1 | 1.5 | 1.5 | 1.5 | 1.5 |
| W (mass %) | 20 | 25 | 10 | 15 | 20 | 25 | 10 | 15 | 20 | 25 |
| Calc. Temp ° C. | 600 | 600 | 600 | 600 | 600 | 600 | 600 | 600 | 600 | 600 |
| P (mass %) | 0.75 | 0.75 | 1 | 1 | 1 | 1 | 1.5 | 1.5 | 1.5 | 1.5 |
| W (mass %) | 20 | 15 | 15 | 20 | 10 | 25 | 15 | 20 | 25 | 10 |
| Calc. Temp ° C. | 700 | 700 | 700 | 700 | 700 | 700 | 700 | 700 | 700 | 700 |
| P (mass %) | 0.75 | 0.75 | 1 | 1 | 1 | 1 | 1.5 | 1.5 | 1.5 | 1.5 |
| W (mass %) | 20 | 15 | 15 | 20 | 10 | 25 | 15 | 20 | 25 | 10 |
| Calc. Temp ° C. | 800 | 800 | 800 | 800 | 800 | 800 | 800 | 800 | 800 | 800 |

TABLE 2

| P (mass %) | 0.025 | 0.05 | 0.05 | 0.05 | 0.1 | 0.1 | 0.1 | | | | | | |
|---|---|---|---|---|---|---|---|---|---|---|---|---|---|
| W (mass %) | 22.5 | 20 | 25 | 30 | 20 | 25 | 30 | | | | | | |
| Calc. Temp ° C. | 700 | 700 | 700 | 700 | 700 | 700 | 700 | | | | | | |
| P (mass %) | 0.025 | 0.05 | 0.05 | 0.05 | 0.1 | 0.1 | 0.1 | | | | | | |
| W (mass %) | 22.5 | 20 | 25 | 30 | 20 | 25 | 30 | | | | | | |
| Calc. Temp ° C. | 800 | 800 | 800 | 800 | 800 | 800 | 800 | | | | | | |
| P (mass %) | 0.025 | 0.05 | 0.05 | 0.05 | 0.1 | 0.1 | 0.1 | 0.25 | 0.25 | 0.25 | 1 | 1 | 1 |
| W (mass %) | 22.5 | 20 | 25 | 30 | 20 | 25 | 30 | 20 | 25 | 30 | 20 | 25 | 30 |
| Calc. Temp ° C. | 850 | 850 | 850 | 850 | 850 | 850 | 850 | 850 | 850 | 850 | 850 | 850 | 850 |

TABLE 3

| Ge | 0.5 | 0.5 | 0.5 | 1 | 1 | 1 | 2.5 | 2.5 | 2.5 |
|---|---|---|---|---|---|---|---|---|---|
| W | 10 | 15 | 20 | 10 | 15 | 20 | 10 | 15 | 20 |
| Calc. Temp ° C. | 600 | 600 | 600 | 600 | 600 | 600 | 600 | 600 | 600 |
| Ge | 0.5 | 0.5 | 0.5 | 1 | 1 | 1 | 2.5 | 2.5 | 2.5 |
| W | 10 | 15 | 20 | 10 | 15 | 20 | 10 | 15 | 20 |
| Calc. Temp ° C. | 700 | 700 | 700 | 700 | 700 | 700 | 700 | 700 | 700 |
| Ge | 0.5 | 0.5 | 0.5 | 1 | 1 | 1 | 2.5 | 2.5 | 2.5 |
| W | 10 | 15 | 20 | 10 | 15 | 20 | 10 | 15 | 20 |
| Calc. Temp ° C. | 800 | 8oo | 800 | 800 | 800 | 800 | 800 | 800 | 800 |

The materials shown in Table 2 were analyzed by X-ray powder diffraction to determine the nature of the species present. Some materials were prepared and analyzed in duplicate, resulting in 48 materials being analyzed by X-ray powder diffraction. The X-ray patterns were obtained using standard X-ray powder diffraction techniques. The radiation source was a high-intensity X-ray tube operated at 45 kV and 35 ma. The diffraction pattern from the copper K-alpha radiation was obtained by appropriate computer based techniques. Flat compressed powder samples were scanned over a 35° (2θ) range from 12.5° to 47.5° (2θ) using a two-dimensional X-ray detector. Interplanar spacings (d) in Angstrom units were obtained from the position of the diffraction peaks expressed as 2θ where θ is the Bragg angle as observed from digitized data. Intensities were determined from the integrated area of diffraction peaks after subtracting background, "$I_o$" being the intensity of the strongest line or peak, and "I" being the intensity of each of the other peaks As will be understood by those skilled in the art, the determination of the parameter 2θ is subject to both human and mechanical error, which in combination can impose an uncertainty of about ±0.4 on each reported value of 2θ and up to ±0.5 on reported values for nanocrystalline materials. This uncertainty is, of course, also manifested in the reported values of the d-spacing, which are calculated from the θ values. This imprecision is general throughout the art and is not sufficient to preclude the differentiation of the present crystalline materials from each other and from the compositions of the prior art.

Figure 9:
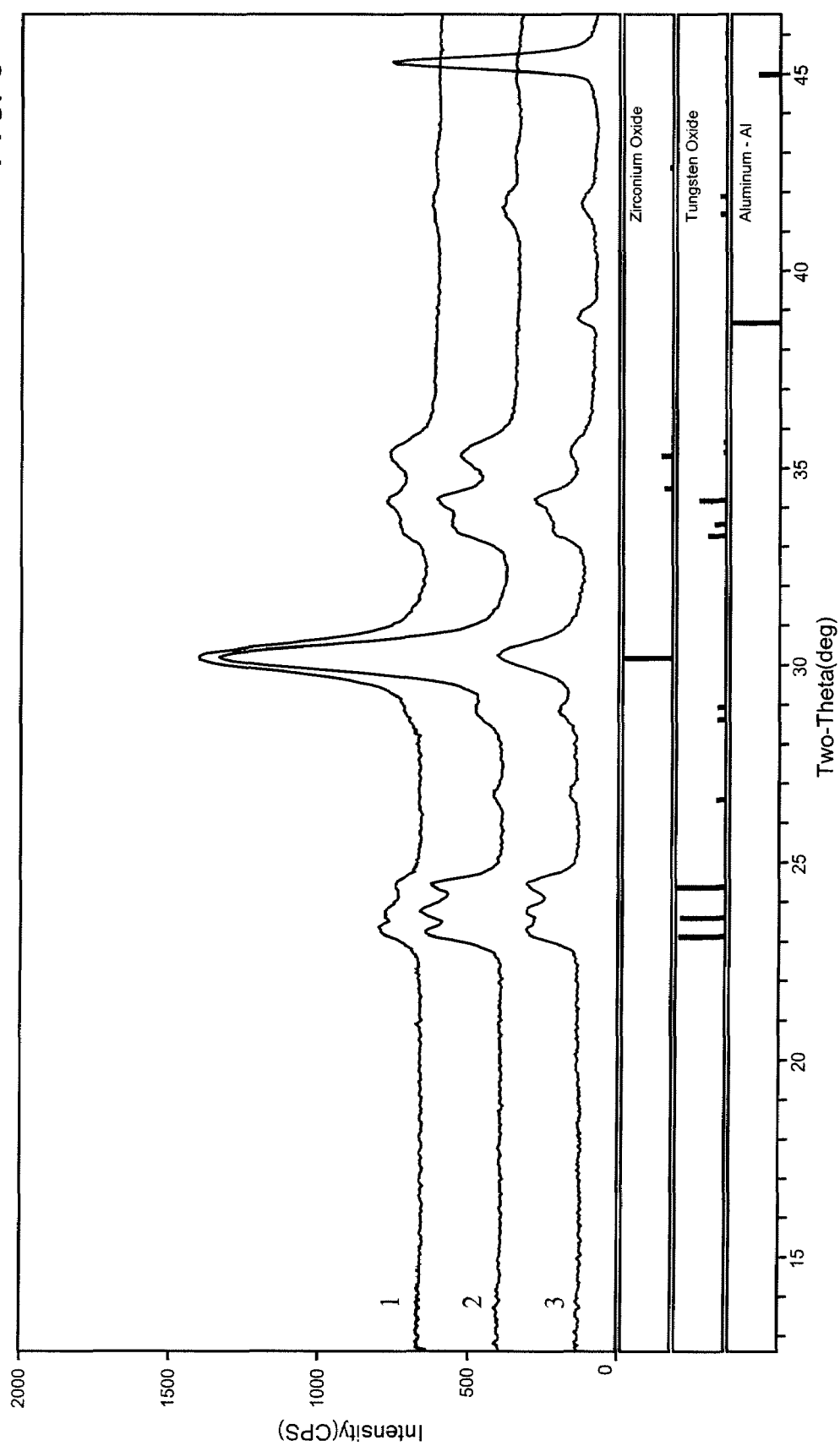
FIG. 9 is a set of three X-ray powder diffraction patterns corresponding to catalysts of Table 2.
Figure 10:
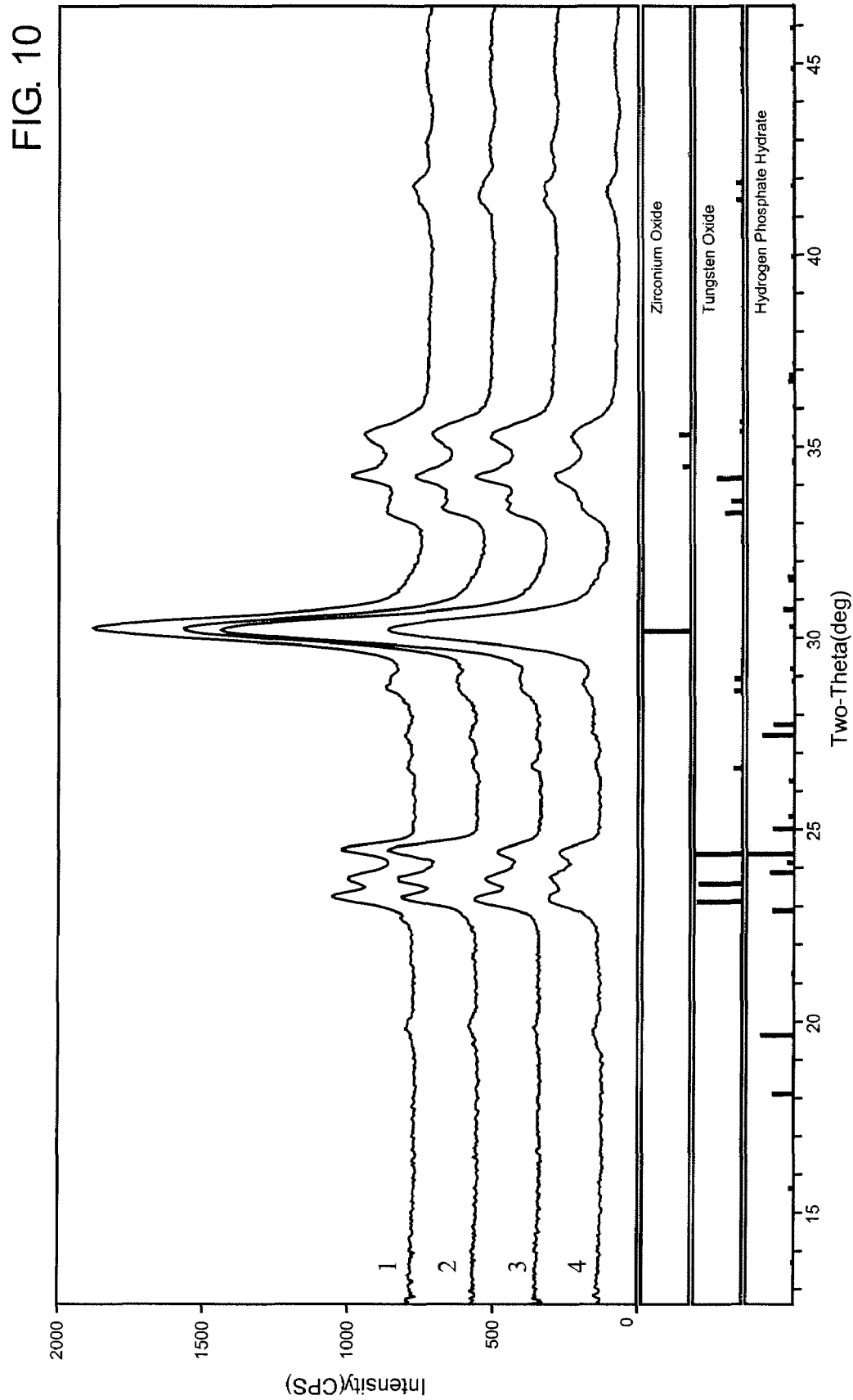
FIG. 10 is a set of four X-ray powder diffraction patterns corresponding to catalysts of Table 2.

In reviewing the X-ray powder diffraction patterns obtained for the materials of Table 2, all samples showed the presence of zirconium oxide, forty-one of the materials showed the presence of tungsten oxide, and seven of the materials showed the presence of hydrogen phosphate hydrate in addition to the presence of tungsten oxide. A few patterns showed aluminum which was due to the sample holder. FIG. 9 shows a representative sampling of the X-ray diffraction patterns of those forty-one materials showing the presence of tungsten oxide. Pattern 1 of FIG. 9 corresponds to a material having 0.5 mass-% of a phosphorus component and 30 mass-% tungsten component, Pattern 2 of FIG. 9 corresponds to a material having no phosphorus component and 30 mass-% tungsten component, and Pattern 3 of FIG. 9 corresponds to a material having 1 mass-% of a phosphorus component and 30 mass-% tungsten component. FIG. 10 shows a representative sampling of the X-ray diffraction patterns of those seven materials showing the presence of hydrogen phosphate hydrate in addition to the presence of tungsten oxide. Pattern 1 of FIG. 10 corresponds to a material having 0.25 mass-% of a phosphorus component and 20 mass-% tungsten component, Pattern 2 of FIG. 10 corresponds to a material having 0.25 mass-% phosphorus component and 25 mass-% tungsten component, Pattern 3 of FIG. 10 corresponds to a material having 0.1 mass-% of a phosphorus component and 20 mass-% tungsten component, and Pattern 4 of FIG. 10 corresponds to a material having 1 mass-% of a phosphorus component and 25 mass-% tungsten component. The component levels above are nominal. No heteropoly anion structures, including Keggin structures, were detected for any of the materials analyzed by X-ray powder diffraction.

EXAMPLE 2

The catalysts of Example 1 were prepared as described above in Example 1. Also, reference catalysts were prepared as described in Example 1 but with the addition of the modifier step being omitted from the preparation. Approximately 95 mg of each sample was loaded into a multi-unit reactor assay. The catalysts were pretreated in air at 450° C. for 6 hours and reduced at 200° C. in $H_2$ for 1 hour. n-Heptane, 8 mol-%, in hydrogen was then passed over the samples at 120° C., 150° C., and 180° C., approximately 1 atm, and 0.3, 0.6, and 1.2 $hr^{-1}$ WHSV (based on heptane only). The products were analyzed using online gas chromatographs.

To exemplify the data, selected results are shown in FIGS. 1-4 for experiments at 180° C., 0.6 $hr^{-1}$ WHSV, and using catalysts comprising 10, 20 and 25 mass-% W, and 0.4 mass-% Pt. The identity of the modifier (or first component), the amount of modifier, the amount of tungsten component, and the calcination temperature are identified along the x-axis of the plots of FIGS. 1-4. Data where the identity of the modifier is listed as "none", corresponds to a reference catalyst containing no modifier. FIG. 1 is a plot of the conversion of heptane achieved by each of the selected catalysts. All of the catalysts indicate activity, with silicon-modified catalysts showing greater conversion than the phosphorus-modified catalysts. However, at low phosphorus levels, activity still trends upward at high levels of tungstate and high calcination temperatures. The optimum tungstate amount appears to be in the range of about 20 to about 25 mass-%. A number of the catalysts of the present invention however, exhibit greater conversion with a calcination at 800° C. than at either 750° C. or 850° C. 850° C. Therefore, a preferred calcination temperature is at 800° C. The component levels above are nominal.

Figure 2:
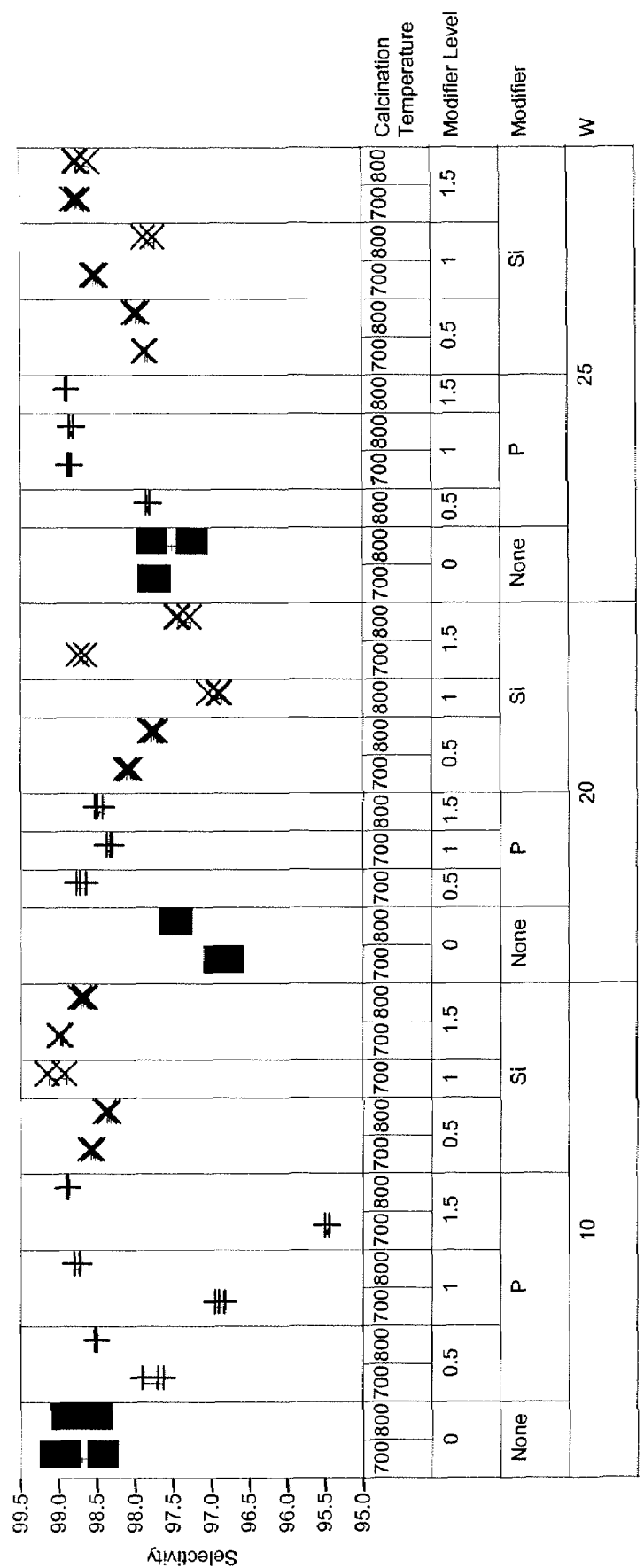
FIG. 2 is a plot of the selectivities of the catalysts of FIG. 1 for n-heptane isomerization.
Figure 3:
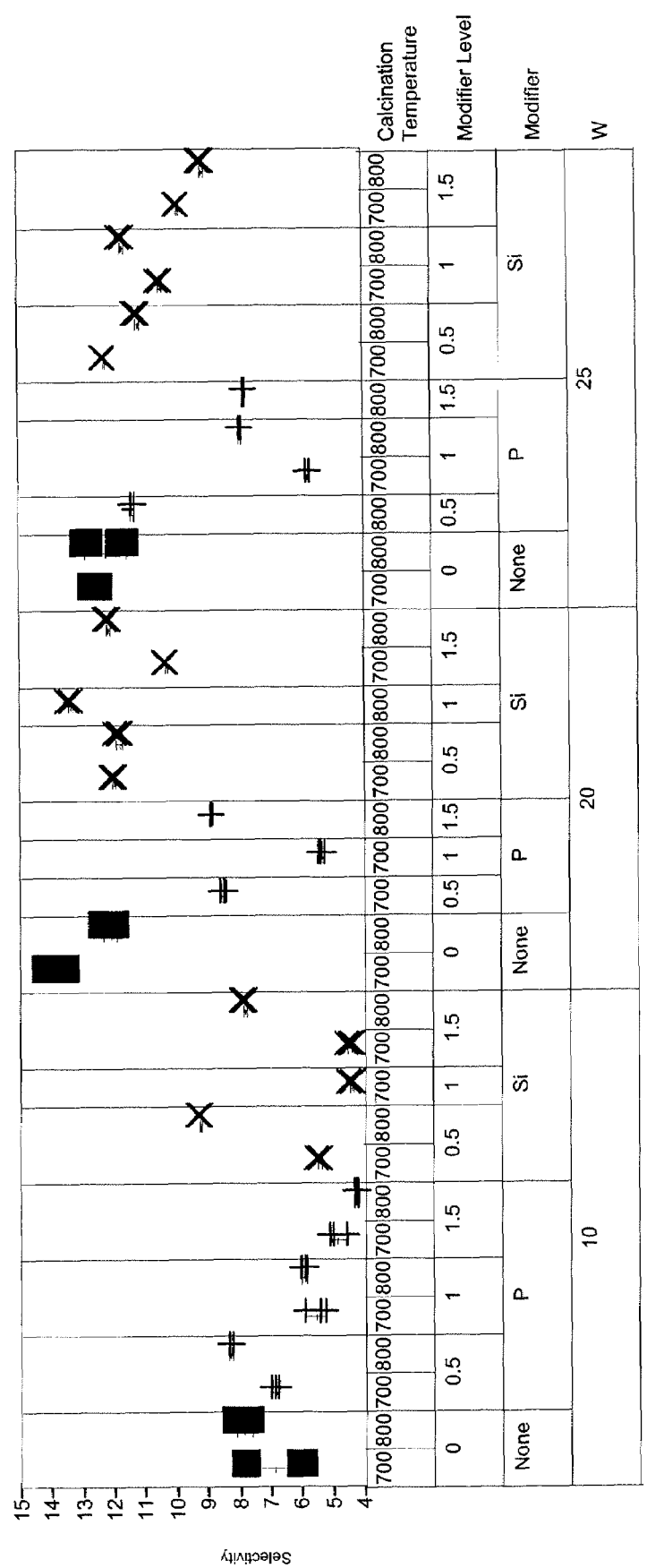
FIG. 3 is a plot of the selectivities of the catalysts of FIG. 1 for the isomerization of n-heptane to 2,2-dimethylpentane and 2,4-dimethylpentane.
Figure 4:
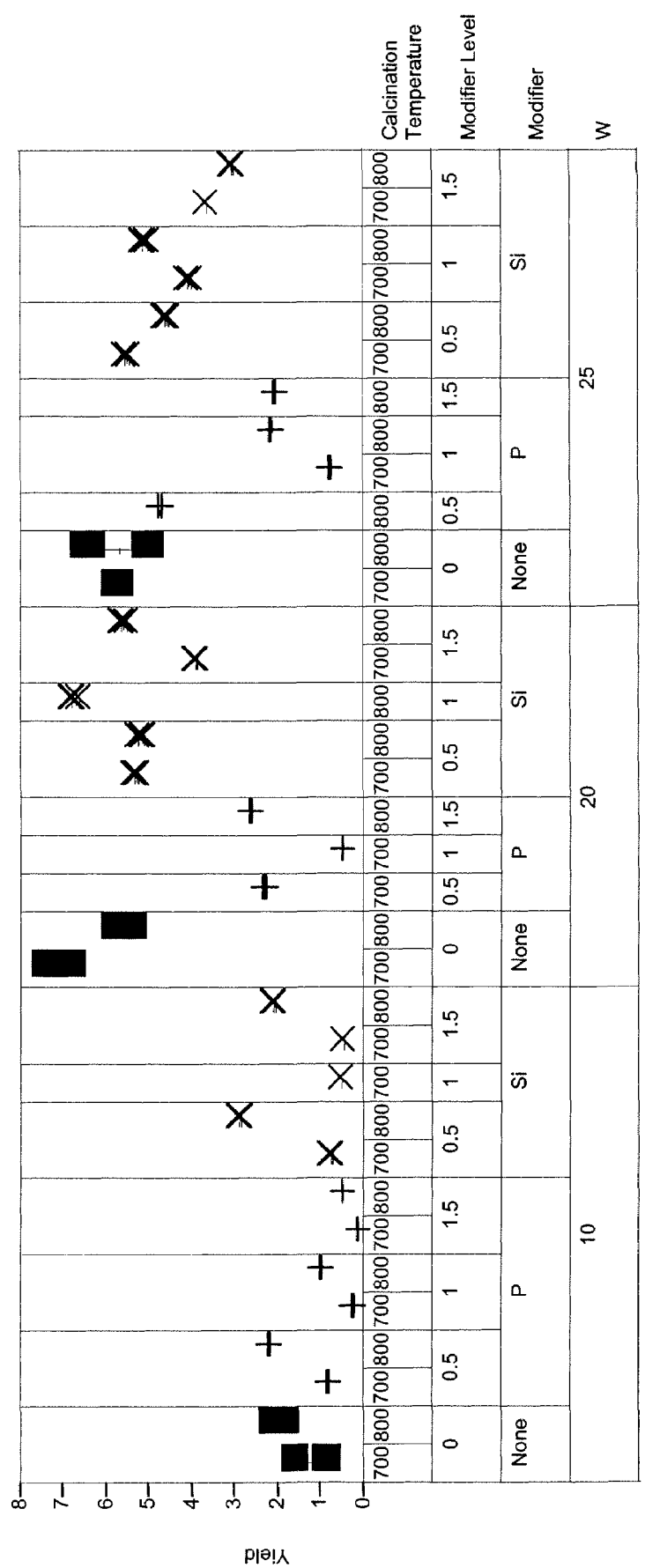
FIG. 4 is a plot of the yields of the catalysts of FIG. 1 for the isomerization of n-heptane to 2,2-dimethylpentane and 2,4-dimethylpentane.

FIG. 2 shows the selectivity of the catalysts for $C_7$ isomerization. This plot demonstrates that even though some cracking is occurring, selectivities to $C_7$ isomerization remain high. FIG. 3 shows the selectivity of the catalysts for $C_7$ isomerization to produce two of the desired dimethyl-branched isomers, 2,2-dimethylpentane and 2,4-dimethylpentane. Again, the data demonstrates that silicon-modified catalysts show superior results and silicon is therefore a preferred modifier over phosphorus. FIG. 4 shows the yield of the catalysts for $C_7$ isomerization to produce two desired dimethyl-branched isomers, 2,2-dimethylpentane and 2,4-dimethylpentane.

Figure 5:
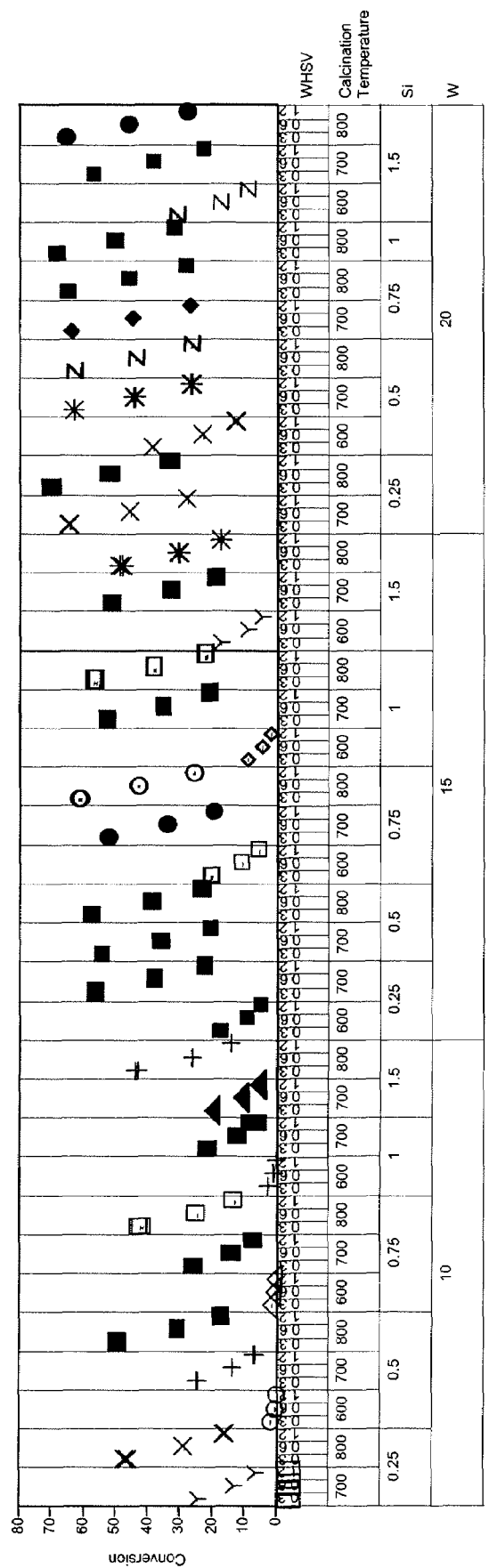
FIG. 5 is a plot of the conversion of n-heptane achieved by selected catalysts made in Example 1 where silicon is a modifier.
Figure 6:
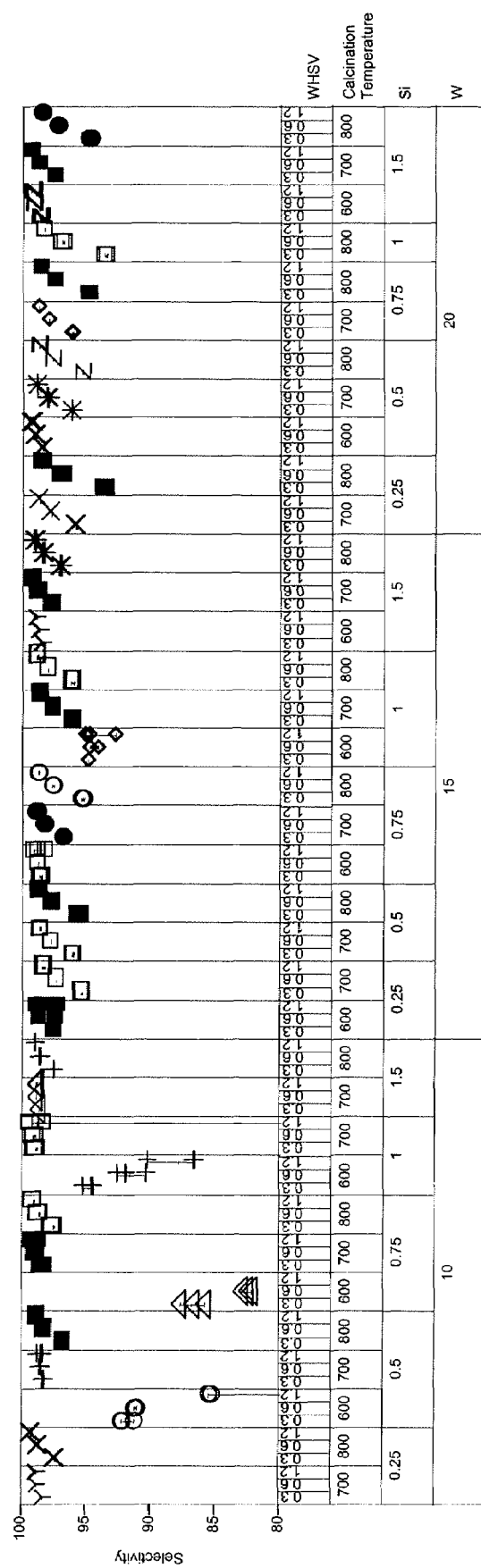
FIG. 6 is a plot of the selectivities of the catalysts of FIG. 5 for n-heptane isomerization.
Figure 7:
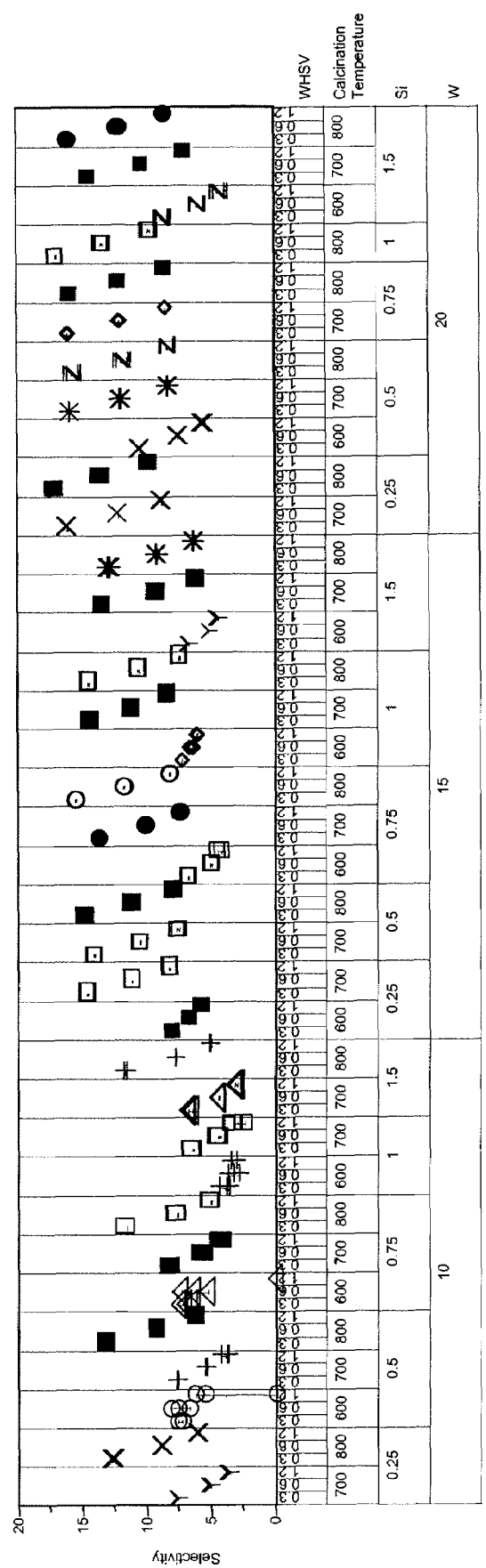
FIG. 7 is a plot of the selectivities of the catalysts of FIG. 5 for the isomerization of n-heptane to 2,2-dimethylpentane and 2,4-dimethylpentane.
Figure 8:
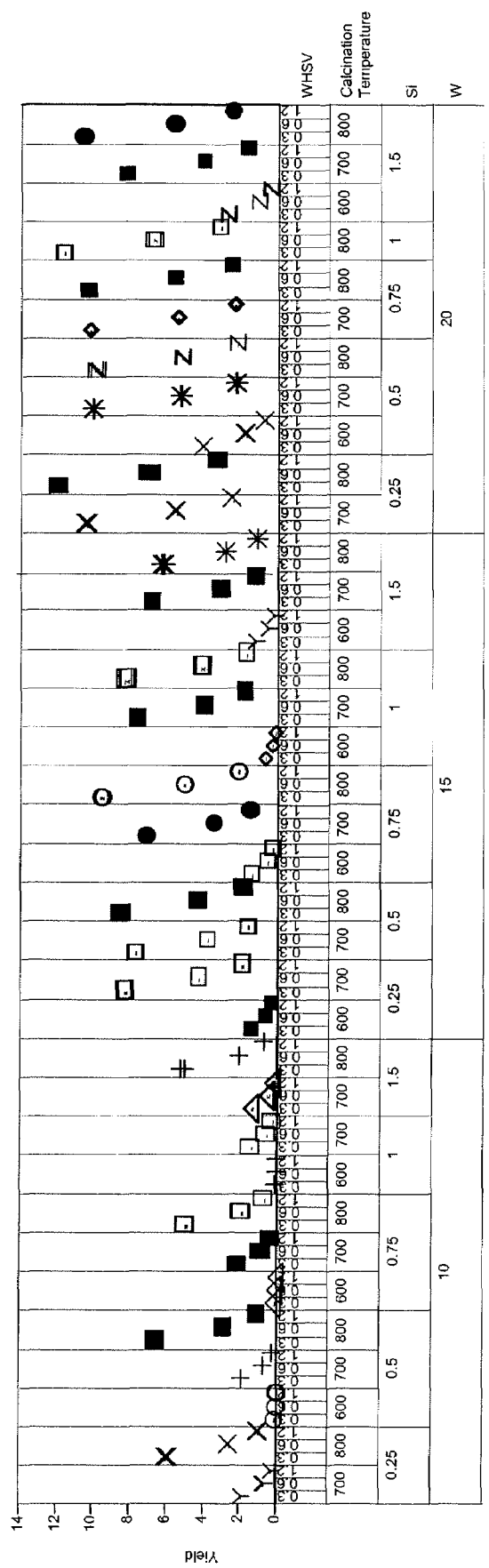
FIG. 8 is a plot of the yields of the catalysts of FIG. 5 for the isomerization of n-heptane to 2,2-dimethylpentane and 2,4-dimethylpentane.

The data discussed above indicates a particular preference for silicon as a modifier over phosphorus. Therefore, FIGS. 5-8 present further selected results of the experiment where silicon was the modifier. On each of FIGS. 5-8, the amount of tungsten on the catalyst, the amount of modifier on the catalyst, the calcination temperature of the catalyst, and the weight hourly space velocity of the run is found on the x-axis. In FIG. 5, the y-axis is the conversion of the n-heptane feed. The plot demonstrates that conversion increases as the amount of tungsten increases, but conversion decreases as the weight hourly space velocity increases. However, with other variables remaining constant, increasing the amount of modifier from 0.25 mass-% to 1.5 mass-% does not have a dramatic effect on the conversion. FIG. 6 demonstrates that the selectivity for $C_7$ isomerization increases with increasing space velocity. However, FIG. 7 shows that the opposite is true when considering the selectivity to two of the desired dimethyl-branched isomers, 2,2-dimethylpentane and 2,4-dimethylpentane. FIG. 8 shows the yield of two of the desired dimethyl-branched isomers, 2,2-dimethylpentane and 2,4-dimethylpentane. In general, the results in FIG. 8 indicate that the yield to the specific dimethylpentane isomers (1) decreases as the space velocity is increased; (2) is highest with a calcination temperature of 800° C.; and (3) is greater at the lower levels of modifiers. The component levels above are nominal.

The invention claimed is:

1. A catalyst consisting essentially of a support comprising a tungstated oxide or hydroxide of at least one of the elements of Group IVB (IUPAC 4) of the Periodic Table; a phosphorous component selected from the group consisting of a phosphorous oxide, a phosphorous hydroxide, a phosphorous halide, a phosphorous oxyhalide, a phosphorous carbonate, a phosphorous nitrate, and a phosphorous sulfate; and at least one platinum-group metal component selected from the group consisting of platinum, palladium, ruthenium, rhodium, iridium, osmium and mixtures thereof.

2. The catalyst of claim 1 wherein the phosphorous component comprises from about 0.01 to about 10 mass-%, on an elemental basis, of the catalyst.

3. The catalyst of claim 1 wherein the platinum-group metal component comprises from about 0.01 to 2 mass-%, on an elemental basis, of the catalyst.

4. The catalyst of claim 1 wherein the element of Group IVB (IUPAC 4) comprises zirconium.

5. The catalyst of claim 1 wherein the catalyst comprises from about 0.5 to about 25 mass-% tungsten on an elemental basis.

6. The catalyst of claim 1 wherein the platinum group-metal component consists essentially of one single metal selected from the platinum-group metal.

7. The catalyst of claim 1 wherein the second platinum-group metal component is platinum.

8. A catalyst consisting essentially of a support comprising a tungstated oxide or hydroxide of at least one of the elements of Group IVB (IUPAC 4) of the Periodic Table; a phosphorous component selected from the group consisting of a phosphorous oxide, a phosphorous hydroxide, a phosphorous halide, a phosphorous oxyhalide, a phosphorous carbonate, a phosphorous nitrate, and a phosphorous sulfate; at least one platinum-group metal component selected from the group consisting of platinum, palladium, ruthenium, rhodium, iridium, osmium and mixtures thereof; and from about 0.1 to 50 mass-% of a refractory inorganic-oxide binder.

9. The catalyst of claim 8 wherein the refractory inorganic-oxide binder comprises an alumina.

10. A catalyst consisting essentially of a support comprising a tungstated oxide or hydroxide of at least one of the elements of Group IVB (IUPAC 4) of the Periodic Table; a phosphorous component selected from the group consisting of a phosphorous oxide, a phosphorous hydroxide, a phosphorous halide, a phosphorous oxyhalide, a phosphorous carbonate, a phosphorous nitrate, and a phosphorous sulfate; at least one platinum-group metal component selected from the group consisting of platinum, palladium, ruthenium, rhodium, iridium, osmium and mixtures thereof; and an additional component selected from the group consisting of at least one Group IVA (IUPAC 14) component, iron, nickel, rhenium, and mixtures thereof.

11. The catalyst of claim 10 wherein the additional component is iron in an amount from about 0.1 to about 5 mass-%.

* * * * *